US010786159B2

(12) United States Patent
Irisawa

(10) Patent No.: US 10,786,159 B2
(45) Date of Patent: Sep. 29, 2020

(54) PHOTOACOUSTIC IMAGE GENERATION APPARATUS AND INSERT

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 708 days.

(21) Appl. No.: 15/397,342

(22) Filed: Jan. 3, 2017

(65) Prior Publication Data
US 2017/0112386 A1 Apr. 27, 2017

Related U.S. Application Data

(63) Continuation of application No. PCT/JP2015/003220, filed on Jun. 26, 2015.

(30) Foreign Application Priority Data

Jul. 8, 2014 (JP) .................................. 2014-140501

(51) Int. Cl.
A61B 5/00 (2006.01)
A61B 8/13 (2006.01)
(Continued)

(52) U.S. Cl.
CPC .......... A61B 5/0097 (2013.01); A61B 5/0084 (2013.01); A61B 5/066 (2013.01);
(Continued)

(58) Field of Classification Search
CPC ... A61B 5/0095; A61B 5/0084; A61B 5/0097; A61B 5/066; A61B 5/6848;
(Continued)

(56) References Cited

U.S. PATENT DOCUMENTS 5,026,350 A * 6/1991 Tanaka .................... A61M 5/32 604/158
2003/0158480 A1* 8/2003 Tornes ................... A61B 90/39 600/437
(Continued)

FOREIGN PATENT DOCUMENTS

CN 103002813 A 3/2013
CN 103623493 A 3/2014
(Continued)

OTHER PUBLICATIONS

Chinese Office Action and English translation for Application No. 201580036416.1, dated May 28, 2019.
(Continued)

Primary Examiner — Carolyn A Pehlke
(74) Attorney, Agent, or Firm — Birch, Stewart, Kolasch & Birch, LLP.

(57) ABSTRACT

An insert includes: an insert body that has an opening and has an inner cavity therein; a light guide member that is inserted into the inner cavity of the insert body and guides light emitted from a light source; a light emitting portion that emits light guided by the light guide member; a light absorption member that generates photoacoustic waves by absorbing the light emitted from the light emitting portion; and a proximal end portion that has an inlet of liquid and a chamber communicating with the inlet and the inner cavity of the insert body. The inner cavity has a space for flow of the liquid, and liquid injected through the inlet is capable of flowing from the opening of the insert body through the chamber and the space for flow of the liquid.

12 Claims, 8 Drawing Sheets

(51) Int. Cl.
*A61B 8/08* (2006.01)
*A61B 8/00* (2006.01)
*A61B 5/06* (2006.01)
*A61B 8/12* (2006.01)

(52) U.S. Cl.
CPC ............ *A61B 8/085* (2013.01); *A61B 8/0841* (2013.01); *A61B 8/12* (2013.01); *A61B 8/13* (2013.01); *A61B 8/445* (2013.01); *A61B 8/4416* (2013.01); *A61B 8/5207* (2013.01); *A61B 8/5246* (2013.01); *A61B 5/0095* (2013.01); *A61B 5/061* (2013.01); *A61B 5/6848* (2013.01); *A61B 8/4477* (2013.01)

(58) Field of Classification Search
CPC ......... A61B 8/0841; A61B 8/085; A61B 8/12; A61B 8/13; A61B 8/4416; A61B 8/445; A61B 8/5207; A61B 8/5246; A61B 8/4477
See application file for complete search history.

(56) References Cited

U.S. PATENT DOCUMENTS

| | | |
|---|---|---|
| 2004/0131299 A1 | 7/2004 | Adoram et al. |
| 2009/0137906 A1* | 5/2009 | Maruyama ............ A61B 8/0841 600/461 |
| 2010/0174197 A1 | 7/2010 | Nakajima et al. |
| 2011/0251490 A1* | 10/2011 | Aharoni ............. A61B 5/02007 600/459 |
| 2013/0060276 A1 | 3/2013 | Hocking |
| 2016/0270667 A1 | 9/2016 | Nakajima et al. |

FOREIGN PATENT DOCUMENTS

| | | |
|---|---|---|
| JP | 57-40632 A | 3/1982 |
| JP | 2009-31262 A | 2/2009 |
| JP | 2013-27513 A | 2/2013 |

OTHER PUBLICATIONS

European Office Action, dated May 9, 2019, for European Application No. 15818484.6.
Chinese Office Action, dated Jan. 4, 2019, for Chinese Application No. 201580036416.1, with an English machine translation.
Extended European Search Report for European Application No. 15818484.6, dated Jun. 26, 2017.
Chinese Office Action, dated Sep. 26, 2019, for Chinese Application No. 201580036416.1, with an English translation thereof.
English Translation of the International Preliminary Report on Patentability (including PCT/IB/373 and PCT/ISA/237) for PCT/JP2015/003220, dated Jan. 10, 2017.

* cited by examiner

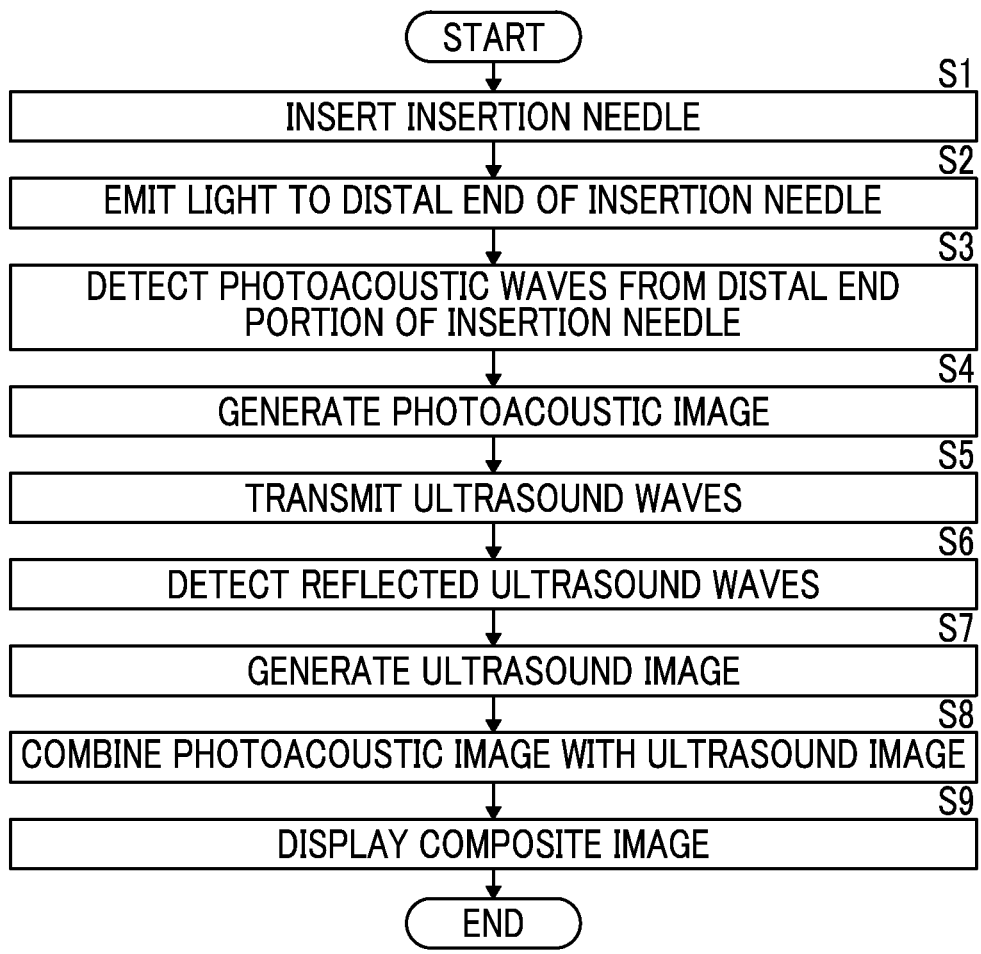
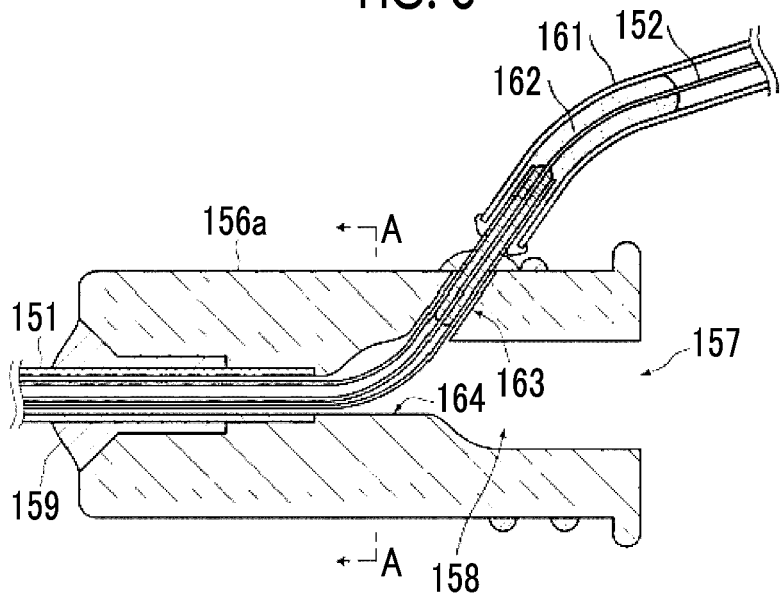

PHOTOACOUSTIC IMAGE GENERATION APPARATUS AND INSERT

CROSS REFERENCE TO RELATED APPLICATIONS

The present application is a Continuation of PCT International Application No. PCT/JP2015/003220 filed on Jun. 26, 2015, which claims priority under 35 U.S.C. § 119(a) to Japanese Patent Application No. 2014-140501 filed on Jul. 8, 2014. Each of the above applications is hereby expressly incorporated by reference, in its entirety, into the present application.

BACKGROUND OF THE INVENTION

1. Field of the Invention

The present invention relates to a photoacoustic image generation apparatus that generates a photoacoustic image based on photoacoustic waves generated by emission of light. In addition, the present invention relates to an insert which is used in such a photoacoustic image generation apparatus and at least a distal end portion of which is inserted into a subject.

2. Description of the Related Art

As a kind of image examination method capable of examining the state of the inside of the body in a non-invasive manner, ultrasonography is known. In ultrasound examination, an ultrasound probe capable of transmitting and receiving ultrasound waves is used. In a case where ultrasound waves are transmitted to the subject (body) from the ultrasound probe, the ultrasound waves propagate through the body to be reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the body using the photoacoustic effect is known. In general, in photoacoustic imaging, pulsed laser light, such as a laser pulse, is emitted into the body. In the body, body tissue absorbs the energy of the pulsed laser light, and ultrasound waves (photoacoustic waves) due to adiabatic expansion due to the energy are generated. By detecting the photoacoustic waves using an ultrasound probe or the like and forming a photoacoustic image based on the detection signal, it is possible to visualize the inside of the body based on the photoacoustic waves.

JP2009-31262A discloses a combination of biological information imaging using photoacoustic waves and treatment using an insertion needle. In JP2009-31262A, an affected part such as a tumor, a part suspected to be an affected part, or the like is found by generating a photoacoustic image and observing the image. In order to examine such a part more precisely or in order to perform injection into the affected part, sampling of cells, injection into the affected part, and the like are performed using an insertion needle, such as an injection needle or a cytodiagnosis needle. In JP2009-31262A, it is possible to perform insertion while observing the affected part using a photoacoustic image.

SUMMARY OF THE INVENTION

Generally, in the insertion of an insertion needle, it is important to know the position of the distal end portion. However, usually, emission of light to the subject is performed from the surface of the subject. In particular, in a case where the distal end of the insertion needle is inserted up to a deep position (for example, a position deeper than 3 cm from the subject surface), light emitted from the subject surface does not sufficiently reach the insertion needle that has been inserted to the deep position. Accordingly, it is difficult to check the position of the distal end of the insertion needle in a photoacoustic image. For example, in a case where the insertion needle allows the injection of medicine, if the position of the distal end cannot be clearly identified, it is difficult to check whether or not the distal end deviates from a desired part into which medicine is to be inserted. These problems are not limited to the insertion needle, and may occur when trying to check the position of an insert, which allows the injection of medicine, using a photoacoustic image.

In view of the above, it is an object of the present invention to provide a photoacoustic image generation apparatus capable of checking the position of an insert, which allows the injection of medicine, on a photoacoustic image, even in a case where the insert is inserted to a deep position from the surface of a subject.

In addition, the present invention provides an insert that is used in the photoacoustic image generation apparatus described above.

In order to achieve the aforementioned object, the present invention provides an insert at least a part of which is inserted into a subject comprising: an insert body that has an opening and has an inner cavity thereinside; a light guide member that is inserted into the inner cavity of the insert body and guides light emitted from a light source; a light emitting portion that emits light guided by the light guide member; a light absorption member that generates photoacoustic waves by absorbing the light emitted from the light emitting portion; and a proximal end portion that has an inlet of liquid and a chamber communicating with the inlet and the inner cavity of the insert body. The inner cavity has a space for flow of the liquid, and liquid injected through the inlet is able to flow from the opening of the insert body through the chamber and the space for flow of the liquid.

The insert of the present invention may further comprise a hollow tube in which the light guide member is housed, which has the light absorption member in a distal end portion, and which is inserted into the inner cavity of the insert body. A diameter of the inner cavity of the insert body may be larger than an outer diameter of the hollow tube, and liquid injected through the inlet may flow from the opening of the insert body through the chamber and a space between the inner cavity of the insert body and the hollow tube.

In the insert of the present invention, the light absorption member may be formed of an adhesive containing a material having a light absorption property mixed thereinto. It is preferable that the adhesive fixes the light guide member at a distal end of the hollow tube and seals the distal end of the hollow tube.

In the insert of the present invention, the hollow tube that is flexible may be inserted in a direction, which is inclined with respect to an extending direction of the insert body, through an insertion hole provided in the proximal end portion, and may be inserted into the inner cavity of the insert body by making a direction change to the extending direction of the insert body in the chamber.

In the insert described above, it is preferable that the chamber has a flat surface, which is for guiding the obliquely inserted hollow tube in a direction of the inner cavity of the insert body, at least between a point where the chamber is connected to the inner cavity of the insert body and a point where a straight line extending in the extending direction of the insert body and a straight line extending in a direction inclined from the insertion hole cross each other.

It is preferable that the flat surface has a groove having a width that decreases toward the inner cavity of the insert body.

The insert may be a needle inserted into the subject. The insert body may form an outer needle, and the hollow tube may form an inner needle.

The insert body may have a protruding portion that protrudes in a convex shape to the inner cavity side.

The insert body may have a plurality of protruding portions along an extending direction of the insert body.

The insert of the present invention may have a recessed portion, which is recessed in a concave shape to the inner cavity side from an outer wall side of the insert body, on a back side of the protruding portion. In this case, the recessed portion may function as a reflection portion that reflects an acoustic wave incident on the insert body in a direction in which the acoustic wave has been incident. The reflection portion may be formed by a recess having an apex of a triangular pyramid as a bottom point.

The light guide member may be an optical fiber. In this case, an end surface of the optical fiber on a light traveling side when viewed from the light source may form the light emitting portion.

In addition, the present invention provides a photoacoustic image generation apparatus comprising: the insert of the present invention described above; an acoustic wave detection means for detecting photoacoustic waves emitted from the insert after at least a part of the insert is inserted into the subject; and photoacoustic image generation means for generating a photoacoustic image based on the photoacoustic waves.

The acoustic wave detection means may be able to further detect reflected acoustic waves of acoustic waves transmitted toward the subject. In this case, the photoacoustic image generation apparatus may further comprise reflected acoustic wave image generation means for generating a reflected acoustic wave image based on the reflected acoustic waves.

According to the photoacoustic image generation apparatus and the insert of the present invention, even in a case where the insert is inserted to a deep position from the surface of the subject, it is possible to check the position of the insert on a photoacoustic image when injecting liquid.

BRIEF DESCRIPTION OF THE DRAWINGS

FIG. 5 is a flowchart showing the operation procedure of the photoacoustic image generation apparatus.

FIG. 6 is a cross-sectional view showing a proximal end portion of an insertion needle according to a second embodiment of the present invention.

DESCRIPTION OF THE PREFERRED EMBODIMENTS

Figure 1:
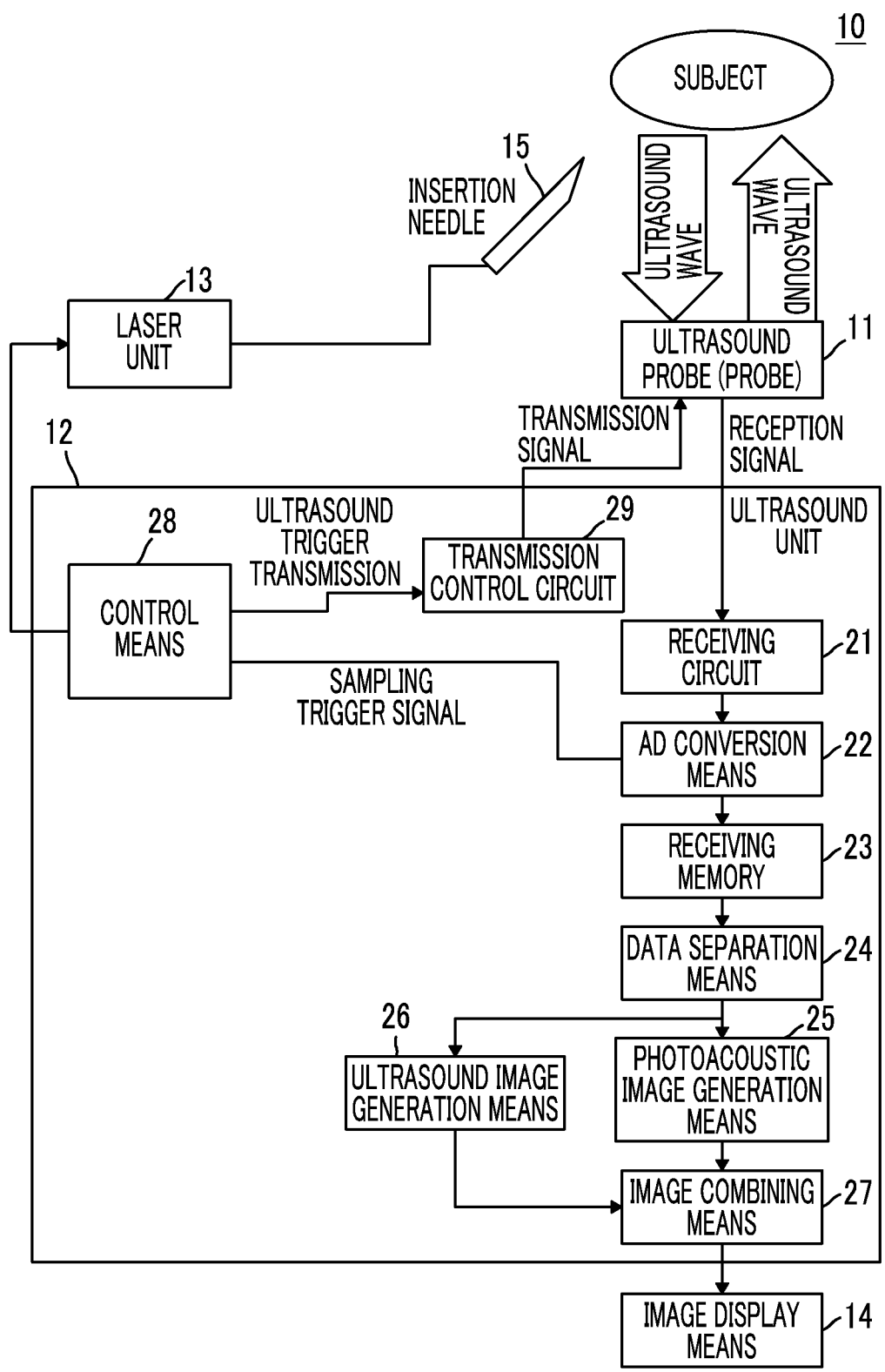
FIG. 1 is a block diagram showing a photoacoustic image generation apparatus according to a first embodiment of the present invention.

Hereinafter, embodiments of the present invention will be described in detail with reference to the diagrams. FIG. 1 shows a photoacoustic image generation apparatus according to a first embodiment of the present invention. A photoacoustic image generation apparatus (photoacoustic image diagnostic apparatus) 10 includes a probe (ultrasound probe) 11, an ultrasound unit 12, a laser unit 13, and an insertion needle 15. In the embodiment of the present invention, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser unit 13 is a light source. The laser unit 13 is a laser diode light source (semiconductor laser light source), for example. Alternatively, the laser unit 13 may be a light amplification type laser light source having a laser diode light source as a seed light source. The type of the laser light source used as the laser unit 13 is not particularly limited. For example, a solid state laser light source using yttrium aluminum garnet (YAG), alexandrite, or the like may be used as the laser unit 13. Laser light emitted from the laser unit 13 is guided to the insertion needle 15, for example, using light guide means, such as an optical fiber. Light sources other than the laser light source may be used.

Figure 2:
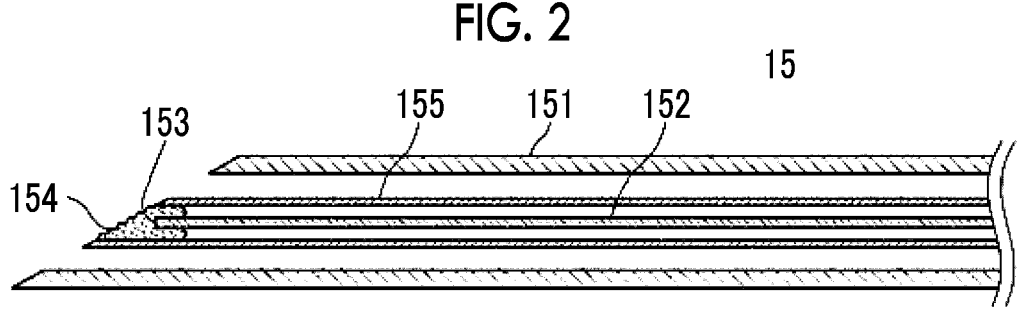
FIG. 2 is a cross-sectional view showing a needle portion of an insertion needle.

In the present embodiment, as an insert at least a distal end portion of which is inserted into the subject, the insertion needle 15 that is inserted into the subject is considered. FIG. 2 shows a cross section of a needle portion of the insertion needle 15. The insertion needle 15 has an insertion needle body 151, a light guide member 152, a light emitting portion 153, a light absorption member 154, and a hollow tube 155. The insertion needle body 151 has an opening at its distal end, and has an inner cavity thereinside. The insertion needle body 151 is formed of, for example, metal, such as stainless steel. The insertion needle body 151 may be formed of, for example, a fluororesin material, such as polytetrafluoroethylene.

The light guide member 152 guides light emitted from the light source. The light guided by the light guide member 152 is emitted from the light emitting portion 153. The light guide member 152 is formed of, for example, an optical fiber, and the end surface of the optical fiber on the light traveling side when viewed from the laser unit 13 forms the light emitting portion 153. The diameter of the optical fiber is 130 μm, for example. For example, laser light of 0.2 mJ is emitted from the light emitting portion 153.

The light absorption member 154 absorbs the light emitted from the light emitting portion 153 to generate photoacoustic waves. As the light absorption member 154, for example, an epoxy resin containing black pigment mixed thereinto, a polyurethane resin, a fluorine resin, or silicone rubber can be used. Alternatively, a metal or oxide having a light absorption property with respect to the wavelength of laser light may be used as the light absorption member 154. For example, oxides, such as an iron oxide, a chromium oxide, and a manganese oxide having a high light absorption property with respect to the wavelength of laser light, can be used as the light absorption member 154. Alternatively, a metal, such as Ti, Pt, pewter, and welded stainless steel, may be used as the light absorption member 154.

The hollow tube 155 is a hollow tube formed of, for example, a metal, such as stainless steel. The hollow tube 155 may be a tube formed of a resin material, such as polyimide. The hollow tube 155 contains the light guide member 152 thereinside, and has the light absorption member 154 in the vicinity of the distal end. The light absorption member 154 clogs the inner cavity of the hollow tube 155 at the distal end of the hollow tube 155, and fixes the end surface (light emitting portion 153) of the light guide member 152 on the light emission side to the vicinity of the distal end of the hollow tube 155.

The hollow tube 155 is inserted into the inner cavity of the insertion needle body 151. The outer diameter of the hollow tube 155 is smaller than the diameter of the inner cavity of the insertion needle body 151. The insertion needle body 151 forms an outer needle, and the hollow tube 155 forms an inner needle. The size of the outer needle is, for example, 20 G (gauge), and the size of the inner needle is, for example, about 29 G or 30 G.

Figure 3:
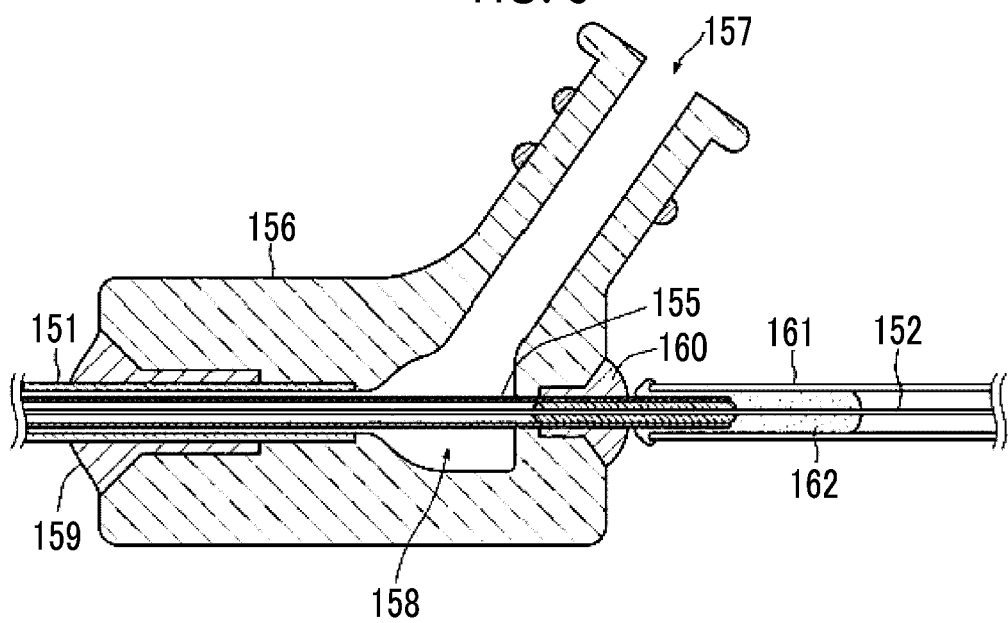
FIG. 3 is a cross-sectional view showing a proximal end portion of the insertion needle.

FIG. 3 shows a cross section of a proximal end portion of the insertion needle 15. A proximal end portion 156 has an inlet 157 and a chamber 158. The proximal end portion 156 is formed of, for example, a resin material, such as polypropylene and polycarbonate polyester. The insertion needle body 151 that forms an outer needle is bonded to the distal end side of the proximal end portion 156 by an adhesive 159. On the other hand, the hollow tube 155 that forms an inner needle is bonded to the rear end side of the proximal end portion 156 by an adhesive 160. As the adhesive 159 and the adhesive 160, it is possible to use an epoxy resin or the like.

The hollow tube 155 is exposed to the back side from the proximal end portion 156, and the exposed portion is covered with a coating tube 161. The coating tube 161 is formed of, for example, polyester. The coating tube 161 is bonded to the hollow tube 155 using an adhesive 162, such as an epoxy resin. The coating tube 161 contains the light guide member 152 thereinside to protect the light guide member 152 between the hollow tube 155 and the laser unit 13 (refer to FIG. 1).

Light emitted from the laser unit 13 is guided to the insertion needle 15 by the light guide member 152, and is emitted from the light emitting portion 153 (refer to FIG. 2) provided at the distal end. Instead of guiding the light from the laser unit 13 to the distal end of the insertion needle 15 using one light guide member 152, an optical connector may be provided in the proximal end portion 156 so that a light guide member for guiding light from the laser unit 13 to the proximal end portion 156 and a light guide member for guiding light from the proximal end portion 156 to the distal end of the insertion needle 15 are separated from each other.

At least some of light components emitted from the light emitting portion 153 are emitted to the light absorption member 154 provided around the light emitting portion 153. Due to the absorption of the emitted light by the light absorption member 154, a photoacoustic wave is generated at the distal end of the insertion needle. Since the light absorption member 154 is present in the vicinity of the distal end of the insertion needle 15, it is possible to generate a photoacoustic wave at one point of the distal end of the insertion needle 15. Since the length of a photoacoustic wave generation source (sound source) is sufficiently shorter than the length of the entire insertion needle, the sound source can be regarded as a point source. Here, the "vicinity" of the distal end of the insertion needle 15 means a position where it is possible to generate photoacoustic waves capable of imaging the position of the distal end of the insertion needle 15 with accuracy, which is required for insertion work, in a case where the light emitting portion 153 and the light absorption member 154 are disposed at the position. For example, the "vicinity" of the distal end of the insertion needle 15 indicates a range of 0 mm to 3 mm toward the proximal end portion side from the distal end having an opening of the insertion needle 15.

The inlet 157 is an inlet of medicine that is liquid. As examples of medicine to be used, anesthetic, drip, anti-cancer agent, ethanol, contrast agent, and saline solution can be considered. A syringe, an infusion tube, or the like is mounted in the inlet 157. The chamber 158 communicates with the inlet 157 and the inner cavity of the insertion needle body 151. Medicine injected through the inlet 157 penetrates into a gap between the inner cavity of the insertion needle body 151, and the hollow tube 155 from the chamber 158. Through the gap, the medicine can flow out from the opening of the insertion needle body 151. The chamber 158 does not need to be molded integrally with the proximal end portion 156 of the insertion needle, and the chamber 158 and the proximal end portion 156 may be separately molded. An angle between the extending direction of the inlet 157 and the extending direction of the hollow tube 155 may be appropriately designed. An angle between the extending direction of the inlet 157 and the extending direction of the hollow tube 155 may be a right angle.

Figure 4:
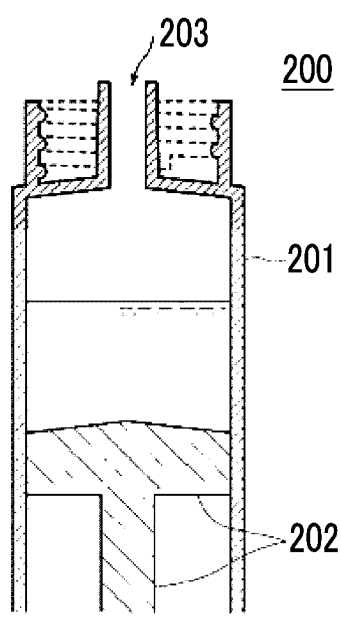
FIG. 4 is a cross-sectional view showing a syringe used for injection of medicine.

FIG. 4 shows a cross section of a syringe used for injection of medicine. A syringe 200 has a medicine receiving space in a syringe body 201. The medicine space communicates with a distal end portion 203 of the syringe. At the time of medicine injection, the distal end portion 203 of the syringe is mounted in the inlet 157 provided in the proximal end portion 156 (refer to FIG. 3). In order to strengthen the mounting, a thread and a recessed portion that suits the thread may be provided around the distal end portion 203 of the syringe and the inlet 157 of the proximal end portion 156, and both may be screwed to each other. Medicine contained in the medicine receiving space is pushed out by a plunger rod 202, and is injected into the inlet 157 through the distal end portion 203 of the syringe.

Referring back to FIG. 1, the probe 11 is acoustic wave detection means, and has a plurality of ultrasound transducers arranged in a one-dimensional manner, for example. The probe 11 detects photoacoustic waves emitted from the light absorption member 154 (refer to FIG. 2) after the insertion needle 15 is inserted into the subject. In addition to the detection of photoacoustic waves, the probe 11 performs transmission of acoustic waves (ultrasound waves) to the subject and reception of reflected acoustic waves (reflected ultrasound waves) of the transmitted ultrasound waves.

The ultrasound unit 12 has a receiving circuit 21, AD conversion means 22, a receiving memory 23, data separation means 24, photoacoustic image generation means 25, ultrasound image generation means 26, image combining means 27, control means 28, and a transmission control circuit 29. The receiving circuit 21 receives a detection signal of the photoacoustic wave detected by the probe 11. In addition, the detection signal of the reflected ultrasound wave detected by the probe 11 is received. The AD conversion means 22 converts the detection signals of the photoacoustic wave and the reflected ultrasound wave, which have been received by the receiving circuit 21, into digital signals. The AD conversion means 22 samples the detection signals of the photoacoustic wave and the reflected ultrasound wave at predetermined sampling periods based on a sampling clock signal having a predetermined period, for example. The AD conversion means 22 stores the sampled detection signals (sampling data) of the photoacoustic wave and the reflected ultrasound wave in the receiving memory 23.

The data separation means 24 separates the sampling data of the detection signal of the photoacoustic wave and the sampling data of the detection signal of the reflected ultrasound wave, which are stored in the receiving memory 23, from each other. The data separation means 24 inputs the sampling data of the detection signal of the photoacoustic wave to the photoacoustic image generation means 25. In addition, the separated sampling data of the reflected ultrasound wave is input to the ultrasound image generation means (reflected acoustic wave image generation means) 26.

The photoacoustic image generation means 25 generates a photoacoustic image based on the detection signal of the photoacoustic wave detected by the probe 11. The generation of a photoacoustic image includes, for example, image reconstruction such as phase matching addition, detection, and logarithmic conversion. The ultrasound image generation means 26 generates an ultrasound image (reflected acoustic wave image) based on the detection signal of the reflected ultrasound wave detected by the probe 11. The generation of an ultrasound image also includes image reconstruction such as phase matching addition, detection, and logarithmic conversion.

The image combining means 27 combines the photoacoustic image and the ultrasound image. The image combining means 27 performs image combination by superimposing the photoacoustic image and the ultrasound image on each other, for example. The composite image is displayed on the image display means 14, such as a display. Without performing image combination, it is also possible to display the photoacoustic image and the ultrasound image on the image display means 14 side by side or to perform switching between the photoacoustic image and the ultrasound image.

The control means 28 controls each unit in the ultrasound unit 12. For example, the control means 28 transmits a trigger signal to the laser unit 13 so that the laser unit 13 emits laser light. In addition, the control means 28 controls the sampling start timing of the photoacoustic wave by transmitting a sampling trigger signal to the AD conversion means 22 in response to the emission of the laser light.

In the case of acquiring an ultrasound image, the control means 28 transmits an ultrasound wave transmission trigger signal for giving an instruction of ultrasound wave transmission to the transmission control circuit 29. In a case where the ultrasound wave transmission trigger signal is received, the transmission control circuit 29 makes the probe 11 transmit ultrasound waves. The control means 28 transmits a sampling trigger signal to the AD conversion means 22 according to the timing of ultrasound wave transmission, thereby starting the sampling of reflected ultrasound waves.

An operator, such as a doctor, connects, for example, a syringe to the inlet 157 of the proximal end portion 156, and inserts the insertion needle 15 into the subject. Since the inner cavity of the insertion needle body 151 is partially clogged with the hollow tube 155, it is possible to prevent a piece of flesh or the like from entering the inner cavity while the needle is being inserted. Accordingly, it is possible to prevent the insertion feeling of the operator from being adversely affected. At this time, the operator can check whether or not the distal end of the insertion needle 15 has been inserted to a desired part by observing an image displayed on the image display means 14. In a case where the opening portion of the insertion needle body 151 reaches blood vessels or the like, blood or the like flows back to the proximal end portion 156 side through the gap between the inner cavity of the insertion needle body 151 and the hollow tube 155. According to the presence or absence of the backflow, it is possible to determine whether or not the needle tip has reached blood vessels or the like. After the needle tip has reached a desired part, the operator injects medicine into the subject through the gap between the inner cavity of the insertion needle body 151 and the hollow tube 155.

FIG. 5 shows the operation procedure of the photoacoustic image generation apparatus. A doctor or the like inserts the insertion needle 15 into the subject (step S1). After inserting the insertion needle 15, the control means 28 of the ultrasound unit 12 transmits a trigger signal to the laser unit 13. In a case where the trigger signal is received, the laser unit 13 starts laser oscillation to emit pulsed laser light. The pulsed laser light emitted from the laser unit 13 is guided to the vicinity of the distal end of the insertion needle 15 by the light guide member 152 (refer to FIGS. 2 and 3), and is emitted from the light emitting portion 153 to be emitted to the light absorption member 154 (step S2).

The probe 11 detects photoacoustic waves generated in the light absorption member 154 within the subject due to the emission of laser light (step S3). The AD conversion means 22 receives detection signals of the photoacoustic waves through the receiving circuit 21, samples the detection signals of the photoacoustic waves, and stores the sampled detection signals in the receiving memory 23. The data separation means 24 transmits the detection signals of the photoacoustic waves stored in the receiving memory 23 to the photoacoustic image generation means 25. The photoacoustic image generation means 25 generates a photoacoustic image based on the detection signals of the photoacoustic waves (step S4).

The control means 28 transmits an ultrasound trigger signal to the transmission control circuit 29. The transmission control circuit 29 makes the probe 11 transmit an ultrasound wave in response to the ultrasound trigger signal (step S5). The probe 11 detects a reflected ultrasound wave after the transmission of an ultrasound wave (step S6). In addition, transmission and reception of ultrasound waves may be performed at separate positions. For example, ultrasound waves may be transmitted from a position different from the probe 11, and reflected ultrasound waves of the transmitted ultrasound waves may be received by the probe 11.

The reflected ultrasound waves detected by the probe 11 are input to the AD conversion means 22 through the receiving circuit 21. Here, the ultrasound wave transmitted from the probe 11 propagates back and forth between the probe 11 and the ultrasound wave reflection position, while the photoacoustic wave propagates through one way from the vicinity of the distal end of the insertion needle 15, which is the generation position, to the probe 11. Accordingly, since the detection of the reflected ultrasound wave requires twice the time for the detection of the photoacoustic wave generated at the same depth position, the sampling clock of the AD conversion means 22 at the time of reflected ultrasound wave sampling may be a half of that at the time of photoacoustic wave sampling. The AD conversion means 22 stores the sampling data of the reflected ultrasound wave in the receiving memory 23.

The data separation means 24 transmits the detection signal of the reflected ultrasound wave stored in the receiving memory 23 to the ultrasound image generation means 26. The ultrasound image generation means 26 generates an ultrasound image based on the detection signal of the reflected ultrasound wave (step S7). The image combining means 27 combines the photoacoustic image generated in step S4 with the ultrasound image generated in step S7 (step S8). An image obtained by the combination in step S8 is displayed on the image display means 14 (step S9).

Here, in the case of performing light emission from the surface of the subject, about 20 mm from the surface is a range where imaging based on the photoacoustic image is possible. In a case where the insertion needle 15 is inserted up to the depth of 50 mm, light emitted from the surface does not sufficiently reach the insertion needle 15. Therefore, it is difficult to image the insertion needle 15 with the light emitted from the surface. In contrast, in the present embodiment, light is guided to the insertion needle 15 by the light guide member 152, and the guided light is emitted to the light absorption member 154 from the light emitting portion 153. The photoacoustic wave generated in the light absorption member 154 is detected by the probe 11, and a photoacoustic image is generated in the ultrasound unit 12. In the present embodiment, since light emission is performed in the vicinity of the distal end of the insertion needle 15, it is possible to emit light to the light absorption member 154 even when the insertion needle is inserted to a deep position. Therefore, it is possible to check the insertion position of the insertion needle 15.

In addition, in a case where light emission from the surface is performed and the insertion needle 15 is inserted at almost a right angle, photoacoustic waves generated in the insertion needle 15 are incident so as to be inclined with respect to the acoustic wave detection surface of the probe 11. For this reason, photoacoustic waves emitted from the insertion needle 15 are less likely to be detected. In contrast, in the present embodiment, photoacoustic waves are generated at one point of the distal end of the insertion needle 15. Therefore, even in a case where the insertion needle 15 is inserted at almost a right angle, it is possible to check the position of the insertion needle 15 in the photoacoustic image.

In the present embodiment, the hollow tube 155 having an outer diameter, which is smaller than the diameter of the inner cavity of the insertion needle body 151, is inserted into the inner cavity of the insertion needle body 151. The proximal end portion 156 has the inlet 157, and the medicine injected through the inlet 157 is injected into the subject from the opening of the insertion needle body 151 through the gap between the inner cavity of the insertion needle body 151 and the hollow tube 155 from the chamber 158. In the present embodiment, since the hollow tube 155 is inserted into the inner cavity of the insertion needle body 151, it is possible to insert the insertion needle 15 smoothly. In addition, when the distal end of the insertion needle 15 reaches blood vessels or the like, blood or the like flows back to the proximal end portion 156 side through the gap between the inner cavity of the insertion needle body 151 and the hollow tube 155. Therefore, it is possible to check whether or not the insertion needle 15 has been inserted into blood vessels or the like according to the presence or absence of the backflow of the blood or the like. In the present embodiment, it is possible to check the insertion position of the insertion needle 15 by observing a photoacoustic image. In addition, since the insertion needle 15 is inserted to a desired position where medicine needs to be injected while observing the image, it is possible to inject the medicine after the insertion to a desired position.

Next, a second embodiment of the present invention will be described. FIG. 6 shows a cross section of a proximal end portion of an insertion needle according to a second embodiment of the present invention. In the insertion needle according to the present embodiment, in the manufacturing process, the hollow tube 155 is inserted into the chamber 158 in a direction, which is inclined with respect to the extending direction of the insertion needle body 151, through an insertion hole 163 provided in a proximal end portion 156a. Others may be the same as in the first embodiment.

The hollow tube 155 is flexible. The hollow tube 155 is inserted into the chamber 158 through the insertion hole 163 provided in the proximal end portion 156a. The insertion hole 163 is inclined with respect to the extending direction of the insertion needle body 151, and the hollow tube 155 is inserted into the chamber 158 in a direction inclined with respect to the extending direction of the insertion needle body 151. The hollow tube 155 inserted into the chamber 158 gradually changes its direction to the extending direction of the insertion needle body 151 in the chamber 158, and is inserted into the inner cavity of the insertion needle body 151. From the point of view of smoothly inserting the hollow tube 155 into the inner cavity of the insertion needle body 151, it is preferable that the inclination (angle) of the insertion hole 163 with respect to the extending direction of the insertion needle body 151 is 45° or less.

The chamber 158 has a flat surface 164, which is for guiding the obliquely inserted hollow tube 155 in the inner cavity direction of the insertion needle body 151, in the traveling direction of the hollow tube 155 inserted through the insertion hole 163. The hollow tube 155 inserted through the insertion hole 163 is bumped against the flat surface 164 to be deflected, thereby changing its direction to the extending direction of the insertion needle body 151. For example, the chamber 158 has the flat surface 164 at least between a point where the chamber 158 is connected to the inner cavity of the insertion needle body 151 and a point where a straight line extending in the extending direction of the insertion needle body 151 and a straight line extending in a direction inclined from the insertion hole 163 cross each other. When inserting the hollow tube 155 into the insertion hole 163, the hollow tube 155 may be inserted with the long side upward in order to prevent the long side end portion (pointed distal end) of the hollow tube from being caught by the flat surface 164. After the distal end of the hollow tube 155 is inserted into the inner cavity of the insertion needle body 151, the hollow tube 155 may be rotated so that the long side is located below.

Figure 7:
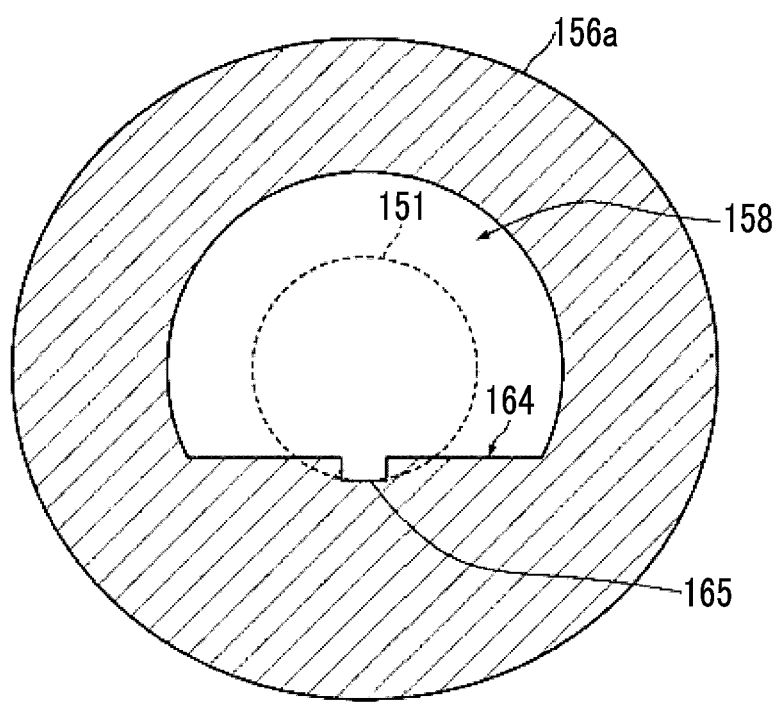
FIG. 7 shows the A-A cross section of FIG. 6.

FIG. 7 shows the A-A cross section of FIG. 6. By the flat surface 164, the bottom surface of the chamber 158 and the lower end of the inner cavity of the insertion needle body 151 are aligned at the same height. The distal end portion of the hollow tube 155 bumped against the bottom surface of the chamber 158 slides on the flat surface 164 to proceed to the inner cavity side of the insertion needle body 151. By providing the flat surface 164, it is possible to connect the chamber 158 and the inner cavity of the insertion needle body 151 to each other without a level difference. Therefore, work for inserting the hollow tube 155, which is inserted through the insertion hole 163, into the inner cavity of the insertion needle body 151 becomes easy.

It is preferable that the flat surface 164 has a groove 165 for guiding the distal end of the hollow tube 155. It is preferable that the depth of the groove 165 is equal to or greater than half of the outer diameter of the hollow tube 155, for example. It is preferable that the width of the groove 165 gradually decreases toward the inner cavity side of the insertion needle body 151 from the inlet 157 side, for example. In the case of providing the groove 165 on the flat surface 164, it is preferable to make the bottom portion of the groove 165 match the lower end of the inner cavity of the insertion needle body 151. In a case where the flat surface 164 has the groove 165, the distal end of the hollow tube 155 inserted obliquely through the insertion hole 163 is guided to the inner cavity of the insertion needle body 151 along the groove 165. Therefore, work for inserting the hollow tube 155 into the inner cavity of the insertion needle body 151 becomes easier. The cross-sectional shape of the groove 165 is not limited to the rectangular shape, and may be a semi-circular shape.

Figure 8:
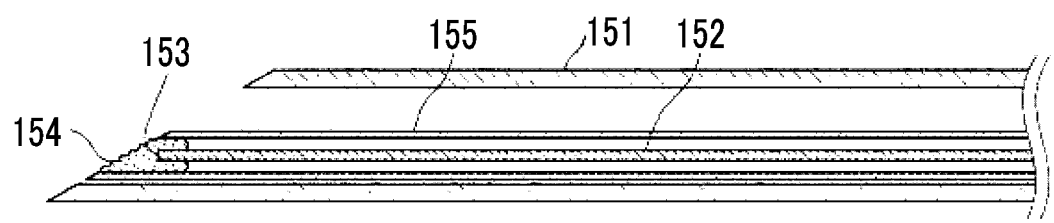
FIG. 8 is a cross-sectional view showing a needle portion of the insertion needle according to the second embodiment.

FIG. 8 shows a cross section of a needle portion of the insertion needle according to the present embodiment. In a case where the hollow tube 155 is inserted obliquely with respect to the chamber 158 and is bent in the chamber 158 to be inserted into the inner cavity of the insertion needle body 151, resilience acts on a portion of the hollow tube 155 that has been inserted into the insertion needle body 151. By the resilience, the hollow tube 155 is pressed against a side of the inner cavity of the insertion needle body 151 opposite a side where the insertion hole 163 is provided in the proximal end portion 156a. In this manner, it is possible to fix the hollow tube 155 to the inner cavity of the insertion needle body 151. In the present embodiment, it is preferable that the proximal end portion 156a has the insertion hole 163 on the short side of the insertion needle body 151 where the distal end is formed at an acute angle. In this case, as shown in FIG. 8, the hollow tube 155 can be pressed against the long side of the insertion needle body 151. As a result, it is possible to generate photoacoustic waves at the more distal end of the insertion needle. Other effects are the same as in the first embodiment.

Figure 9A:
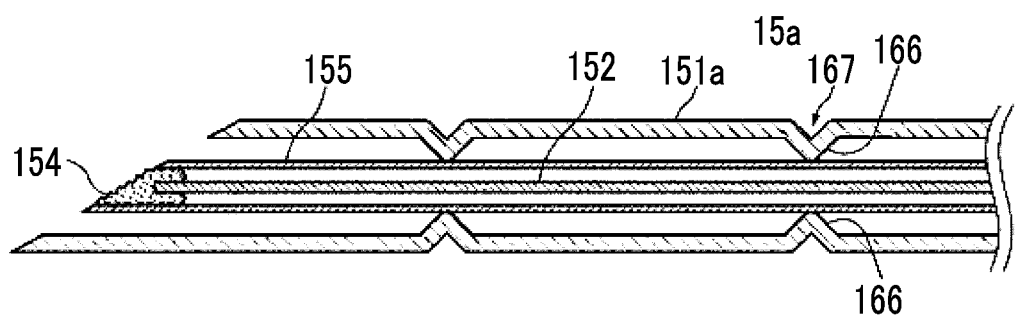
FIG. 9A is a cross-sectional view of an insert according to a third embodiment of the present invention along the extending direction of the insert body.
Figure 9B:
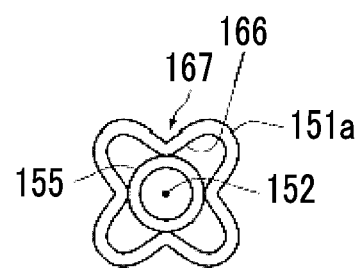
FIG. 9B is a cross-sectional view of a portion of the insert according to the third embodiment, in which a protruding portion is present, in a direction perpendicular to the extending direction.

Next, a third embodiment of the present invention will be described. FIG. 9A shows a cross section of an insert according to the third embodiment of the present invention along the extending direction of the insert body, and FIG. 9B shows a cross section of a portion, in which a protruding portion is present, in a direction perpendicular to the extending direction. An insertion needle 15a according to the present embodiment is different from the insertion needle 15 according to the first embodiment in that an insertion needle body 151a has a protruding portion 166 that protrudes in a convex shape to the inner cavity side. Others may be the same as in the first embodiment.

The insertion needle body 151 has the protruding portion 166 protruding in a convex shape to the inner cavity side. As shown in FIG. 9A, the insertion needle body 151 has a plurality of protruding portions 166 along the extending direction, for example. The plurality of protruding portions 166 are arranged at equal intervals along the extending direction of the insertion needle body 151, for example. For example, when the length of the insertion needle body 151 is 10 cm, the insertion needle body 151 has the plurality of protruding portions 166 that are arranged at intervals of about 1 cm to 2 cm. For example, as shown in FIG. 9B, the insertion needle body 151 has the plurality of protruding portions 166 along the circumferential direction. The number of protruding portions 166 along the circumferential direction is preferably three or more, and more preferably four or more. In a portion where the protruding portion 166 is present, the diameter of the inner cavity of the insertion needle body 151 is reduced by the amount of protrusion of the protruding portion 166.

The protruding portion 166 can be formed by denting the insertion needle body 151 in a concave shape to the inner cavity side from the outside, for example. For example, the protruding portion 166 is formed by pressing a convex mold against the insertion needle body 151 from the outside so that the insertion needle body 151 is partially dented to the inner cavity side. A place dented in a concave shape outside the insertion needle body 151 is a recessed portion 167. Pressing of the convex mold against the insertion needle body 151 may be performed before inserting the hollow tube 155 into the inner cavity. Alternatively, instead of the hollow tube 155, the protruding portion 166 and the recessed portion 167 may be formed by pressing the convex mold against the insertion needle body 151 in a state in which a tube simulating a hollow tube, which has an outer diameter slightly larger than the outer diameter of the hollow tube 155 and which is rigid so as not be deformed by the pressing of a mold, has been inserted into the inner cavity.

Figure 10A:
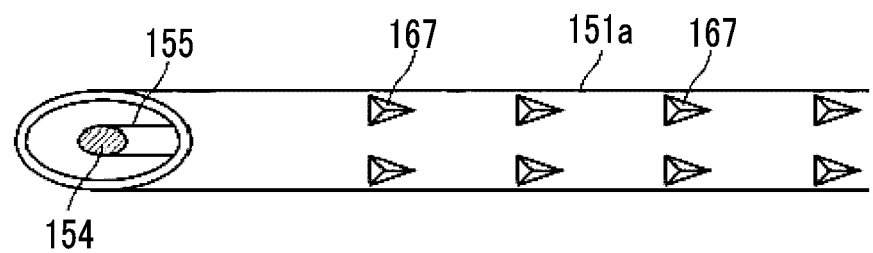
FIG. 10A is a diagram showing the appearance of the insertion needle body.
Figure 10B:
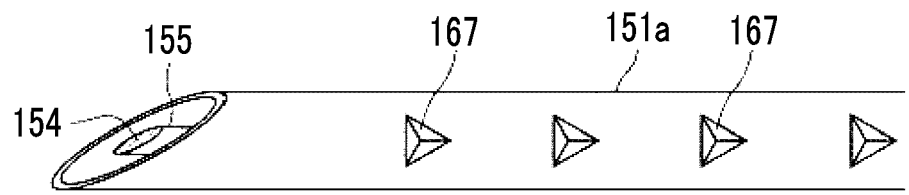
FIG. 10B is a diagram showing the appearance of the insertion needle body.

The recessed portion 167 formed outside the insertion needle body 151 may be made to function as a reflection portion that reflects an ultrasound wave incident on the insertion needle body 151 in a direction in which the ultrasound wave has been incident. FIGS. 10A and 10B show the appearance of the insertion needle body 151. FIG. 10A is a diagram when the insertion needle body 151 is viewed from the short side, and FIG. 10B is a diagram when the insertion needle body 151 is viewed from the side. For example, the recessed portion 167 functioning as a reflection portion is formed by a recess having the apex of the triangular pyramid as its bottom point. In this case, the recessed portion 167 serves as a corner cube reflector to reflect the incident ultrasound wave in the incidence direction. In this case, since the ultrasound wave transmitted from the probe 11 (refer to FIG. 1) is reflected in the direction of the probe 11 in the recessed portion 167, the reflected ultrasound wave detected by the probe 11 is strengthened, and the recessed portion 167 is emphasized in the ultrasound image.

In the present embodiment, the insertion needle body 151 has the protruding portion 166 on the inner cavity side. In a place where the protruding portion 166 is present, the diameter of the inner cavity is reduced by the amount of protrusion of the protruding portion 166. Accordingly, a range in which the hollow tube 155 inserted into the inner cavity moves is restricted. In particular, by providing preferably three or more protruding portions 166, more preferably four or more protruding portions 166, along the circumferential direction, it is possible to suppress a situation in which the hollow tube 155 moves within the inner cavity of the insertion needle body 151 when inserting the insertion needle 15a or when injecting medicine. In addition, by forming the plurality of protruding portions 166, for example, at equal intervals along the extending direction of the insertion needle body 151, it is possible to further restrict the movement of the hollow tube 155.

In the case of forming the protruding portion 166, which protrudes to the inner cavity side of the insertion needle body 151, by denting the insertion needle body 151 partially in a concave shape, the recessed portion 167 is formed on the opposite side to the protruding portion 166. By forming the recessed portion 167 in a shape that strengthens the reflected ultrasound wave detected in the probe 11, it is possible to highlight the recessed portion 167 in the ultrasound image. For example, by forming a plurality of recessed portions 167 along the extending direction of the insertion needle body 151, portions highlighted in the ultrasound image are discretely arranged. As a result, it is possible to visually recognize the insertion needle body 151.

In each of the above embodiments, a case has been described in which the probe 11 detects both the photoacoustic wave and the reflected ultrasound wave. However, a probe used to generate an ultrasound image and a probe used to generate a photoacoustic image do not necessarily need to be the same. The photoacoustic wave and the reflected ultrasound wave may be detected by separate probes. Either the detection (sampling) of the photoacoustic wave or the detection (sampling) of the reflected ultrasound wave may be performed first.

The insertion needle is not limited to being percutaneously inserted into the subject from the outside of the subject, and a needle for ultrasound endoscope may be used. The light guide member 152 and the light absorption member 154 may be provided in the needle for ultrasound endoscope, light may be emitted to the light absorption member 154 provided in the distal end portion of the needle, and photoacoustic waves may be detected to generate a photoacoustic image. In this case, it is possible to insert the needle for ultrasound endoscope while checking the position of the distal end portion of the needle for ultrasound endoscope by observing the photoacoustic image. The photoacoustic wave generated in the distal end portion of the needle for ultrasound endoscope may be detected using a probe for body surface, or may be detected using a probe built into the endoscope.

In each of the embodiments described above, an insertion needle has been considered as an insert. However, the insert is not limited thereto. The insert may be a catheter inserted into the blood vessel. In addition, the insert may be an indwelling needle. The hollow tube 155 that forms an inner needle does not necessarily need to be fixed to the proximal end portion 156 using an adhesive, and the hollow tube 155 may be provided so as to be removable from the proximal end portion 156. In a case where the hollow tube 155 is provided so as to be removable from the proximal end portion 156, injection of medicine may be performed in a state in which the hollow tube 155 has been removed. The insertion port of the hollow tube 155 may be formed in a structure having a plug attached thereto. After removing the hollow tube 155 from the proximal end portion 156, the insertion port of the hollow tube 155 may be used as an inlet of another medicine.

Although an example in which the hollow tube 155 is disposed at the center of the insertion needle body 151 is shown in the first embodiment, the present invention is not limited thereto. The position of the center of the hollow tube 155 and the position of the center of the insertion needle body 151 do not need to match each other, and the hollow tube 155 may be disposed on the long side of the insertion needle body 151 as in the second embodiment. In the third embodiment, similarly, the position of the center of the hollow tube 155 and the position of the center of the insertion needle body 151 do not need to match each other.

Figure 11A:
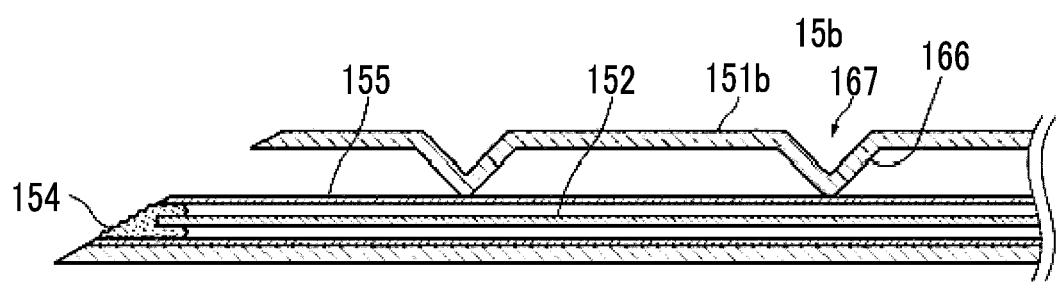
FIG. 11A is a cross-sectional view of an insert according to a modification example of the present invention along the extending direction of the insert body.
Figure 11B:
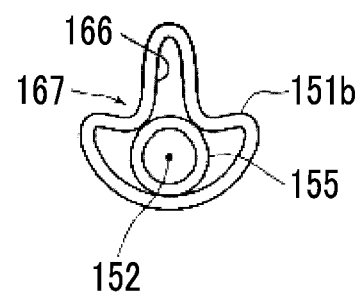
FIG. 11B is a cross-sectional view of a portion of the insert according to the modification example, in which a protruding portion is present, in a direction perpendicular to the extending direction.

FIG. 11A shows a cross section of an insert according to a modification example of the present invention along the extending direction of the insert body, and FIG. 11B shows a cross section of a portion, in which a protruding portion is present, in a direction perpendicular to the extending direction. In the modification example shown in FIGS. 11A and 11B, the insertion needle body of an insertion needle 15b has two protruding portions 166 per one place in the circumferential direction. Others may be the same as in the third embodiment.

By providing the protruding portion 166 on the short side of the insertion needle body 151, the hollow tube 155 can be held on the long side rather than the center of the inner cavity of the insertion needle body 151. In the case of providing the protruding portion 166 in the insert according to the second embodiment that presses the hollow tube 155 against the long side of the insertion needle body 151 using the deflection of the hollow tube 155, the protruding portion 166 may be provided on one side of the inner cavity of the insertion needle body 151 to restrict the movement of the hollow tube 155 as shown in FIGS. 11A and 11B.

In each of the above embodiments, an example has been described in which the insertion needle 15 has the hollow tube 155 inserted into the inner cavity of the insertion needle body 151. However, the present invention is not limited thereto. Instead of inserting the light guide member 152 into the inner cavity of the insertion needle body 151 in a state in which the light guide member 152 is housed in the hollow tube 155, the light guide member 152 itself may be inserted into the inner cavity of the insertion needle body 151. In this case, the light guide member 152 serves as an inner needle. Since the outer diameter of the light guide member 152 is smaller than the diameter of the inner cavity of the insertion needle body 151, medicine injected through the inlet 157 can flow from the opening through the space between the inner cavity of the insertion needle body 151 and the light guide member 152. In the case of inserting the light guide member 152 into the inner cavity of the insertion needle body 151 without using the hollow tube 155, an optical fiber having a larger diameter than in the case where the hollow tube 155 is used can be used as the light guide member 152.

Figure 12:
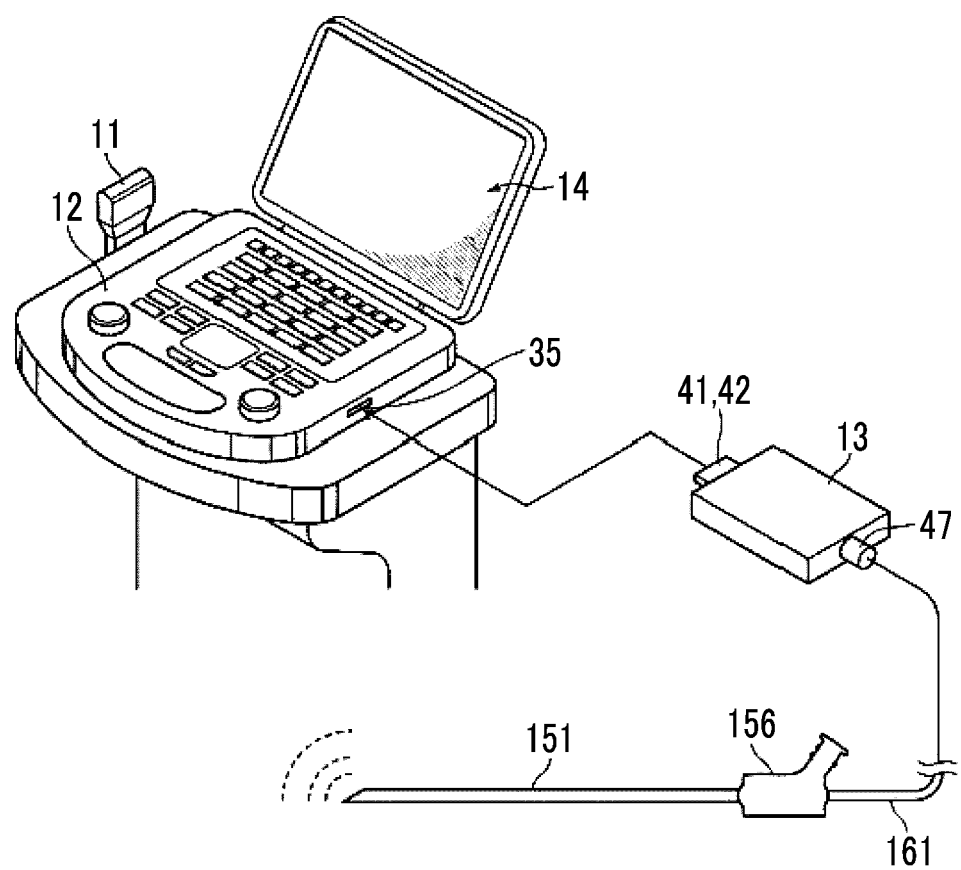
FIG. 12 is a diagram showing the appearance of a photoacoustic image generation apparatus including a laser unit.

Finally, FIG. 12 shows the appearance of a photoacoustic image generation apparatus. The probe 11 is connected to the ultrasound unit 12. The ultrasound unit 12 is configured as an integrated device including the image display means 14. The ultrasound unit 12 typically has a processor, a memory, a bus, and the like. A program regarding photoacoustic image generation is installed in the ultrasound unit 12.

The ultrasound unit 12 has a USB port 35. A USB connector including a power input terminal 41 and a trigger input terminal 42 of a laser unit 13 is inserted into the USB port 35. In a case where the laser unit 13 is a card-sized small and lightweight device, it is possible to hold the USB connector by inserting the USB connector into the USB port of the ultrasound unit 12. The USB port 35 may have any shape allowing a normal USB connector to be inserted thereinto, and does not need to be a port for transmitting and receiving a signal conforming to the normal USB standard. In the USB port, a signal line for a trigger signal may be included instead of a digital signal line. That is, the USB port 35 may be a USB type port as a connector having a total of four terminals of two lines for power supply and two lines for triggering. By using the signal line for a trigger signal instead of the digital signal line, it becomes easy to take trigger synchronization with the laser unit 13.

One end of the optical fiber that forms the light guide member of the insertion needle 15 is connected to a light output terminal 47 of the laser unit 13. The optical fiber is inserted into the light output terminal 47, and is held by spring force or the like. If the operator applies a strong force to the light output terminal 47, for example, by pulling the insertion needle 15, the optical fiber exits from the light output terminal 47. Accordingly, it is possible to prevent the optical fiber from being broken. In addition, by making it possible to directly insert or remove the optical fiber into or from the light output terminal 47, there is an effect that the cost can be reduced without providing a connector in the optical fiber extending from the insertion needle 15.

Pulse energy of the pulsed laser light output from the laser unit 13 can be set to 6.4 µJ if the core diameter of the optical fiber forming the light guide member 152 is 200 µm. The pulse energy of the pulsed laser light can be set to 2.0 µJ if the core diameter of the optical fiber is 100 µm. The pulse time width can be set to 80 ns.

In FIG. 12, the light output terminal 47 is provided on a surface opposite to a surface on which the USB connector including the power input terminal 41 and the trigger input terminal 42 is present. However, it is preferable that the light output terminal 47 is provided on a surface perpendicular to the surface on which the USB connector is present. In a case where the USB connector and the light output terminal 47 are provided on the opposite surfaces, if the laser unit 13 is pulled when the operator moves the insertion needle 15, the USB connector may exit from the USB port 35. In contrast, in a case where the USB connector and the light output terminal 47 are provided on the surfaces perpendicular to each other, the USB connector is difficult to exit from the USB port 35 even if the laser unit 13 is pulled.

In FIG. 12, the laser unit 13 is directly connected to the USB port 35. However, the present invention is not limited thereto, and the USB port 35 and the laser unit 13 may be connected to each other using an extension cable or the like. The trigger input terminal 42 does not need to be included in the USB connector, and the laser unit 13 may acquire a trigger signal from a connector (terminal) different from the USB port 35. For example, a trigger signal may be acquired from a connector for electrocardiogram (ECG) synchronization attached to the normal ultrasound system. Alternatively, a trigger signal may be acquired from some terminals of the connector of the probe.

While the present invention has been described based on the preferred embodiment, the photoacoustic image generation apparatus and the insert of the present invention are not limited to the above embodiments, and various modifications and changes in the configuration of the above embodiment are also included in the range of the present invention.

What is claimed is:

1. An insert at least a part of which is configured to be inserted into a subject, comprising:
    an insert body that has an opening and has an inner cavity thereinside;
    a light guide member that is inserted into the inner cavity of the insert body and guides light emitted from a light source;
    a light emitting portion that emits light guided by the light guide member;
    a light absorption member that generates photoacoustic waves by absorbing the light emitted from the light emitting portion;
    a proximal end portion that has an inlet of liquid and a chamber communicating with the inlet and the inner cavity of the insert body; and
    a hollow tube in which the light guide member is housed, which has the light absorption member in a distal end portion, and which is inserted into the inner cavity of the insert body, wherein
    a diameter of the inner cavity of the insert body is larger than an outer diameter of the hollow tube,
    the inner cavity has a space for flow of the liquid between the inner cavity of the insert body and the hollow tube,
    liquid injected through the inlet is able to flow from the opening of the insert body through the chamber and the space for flow of the liquid in a state in which the light guide member is inserted in the inner cavity,
    the hollow tube is flexible,
    the hollow tube extends into the chamber in a direction, which is inclined with respect to an extending direction of the insert body, through an insertion hole provided in the proximal end portion,
    the chamber has a flat surface, which is for guiding the hollow tube in a direction of the inner cavity of the insert body, at least between a point where the chamber is connected to the inner cavity of the insert body and a point where a straight line extending in the extending direction of the insert body and a straight line extending in a direction inclined from the insertion hole cross each other, and
    a part of the hollow tube that is closer to the distal end than a part located in the chamber extends into the inner cavity of the insert body.

2. The insert according to claim 1, wherein
    the light absorption member is formed of an adhesive containing a material having a light absorption property mixed thereinto, and
    the adhesive fixes the light guide member at a distal end of the hollow tube and seals the distal end of the hollow tube.

3. The insert according to claim 1, wherein the flat surface has a groove having a width that decreases toward the inner cavity of the insert body.

4. The insert according to claim 1, wherein
    the insert functions as a needle, and
    the insert body functions as an outer needle, and the hollow tube functions as an inner needle.

5. The insert according to claim 1, wherein the insert body has a protruding portion that protrudes in a convex shape to the inner cavity side.

6. The insert according to claim 5, wherein the insert body has a plurality of protruding portions along an extending direction of the insert body.

7. The insert according to claim 5, wherein a recessed portion that is recessed in a concave shape to the inner cavity side from an outer wall side of the insert body is provided on a back side of the protruding portion.

8. The insert according to claim 7, wherein the recessed portion functions as a reflection portion that reflects an acoustic wave incident on the insert body in a direction in which the acoustic wave has been incident.

9. The insert according to claim 8, wherein the reflection portion is formed by a recess having an apex of a triangular pyramid as a bottom point.

10. The insert according to claim 1, wherein
    the light guide member is an optical fiber, and
    an end surface of the optical fiber on a light traveling side when viewed from the light source forms the light emitting portion.

11. A photoacoustic image generation apparatus, comprising:
    the insert according to claim 1;

an acoustic wave detector configured to detect photoacoustic waves emitted from the insert after at least a part of the insert is inserted into the subject; and photoacoustic image generator configured to generate a photoacoustic image based on the photoacoustic waves.

12. The photoacoustic image generation apparatus according to claim 11, wherein the acoustic wave detector is further configured to detect reflected acoustic waves of acoustic waves transmitted toward the subject, and a reflected acoustic wave image generator configured to a reflected acoustic wave image based on the reflected acoustic waves is further provided.

* * * * *